United States Patent [19]
Warner et al.

[11] Patent Number: 5,078,999
[45] Date of Patent: Jan. 7, 1992

[54] METHOD OF TREATING SYSTEMIC LUPUS ERYTHEMATOSUS

[75] Inventors: Linda M. Warner, North Brunswick, N.J.; Laurel M. Adams, Durham, N.C.

[73] Assignee: American Home Products Corporation, New York, N.Y.

[21] Appl. No.: 660,470

[22] Filed: Feb. 22, 1991

[51] Int. Cl.⁵ .................. A61K 35/74; A61K 31/44
[52] U.S. Cl. .................................... 424/122; 514/291
[58] Field of Search ................... 514/291; 424/122

[56] References Cited
U.S. PATENT DOCUMENTS
3,929,992 12/1975 Sehgal et al. ..................... 424/122

OTHER PUBLICATIONS

Chemical Abstracts, 87:111825p, (1977).
Scand. J. Immunol., 24:405, (1986).
J. Immunol., 138:157, (1987).
Clin. Immunol. Immunopath, 51:110, (1989).
Can. J. Physiol. Pharmacol., 55, 48, (1977).
FASEB 3,3411, (1989).
Med. Sci. Res., 17:877, (1989).
FASEB Journal, 4(3):A358, abstract, 535, 537, (1990).

Primary Examiner—Jerome D. Goldberg
Attorney, Agent, or Firm—Richard K. Jackson

[57] ABSTRACT

This invention provides a method of treating systemic lupus erythematosus in a mammal in need thereof which comprises administering an effective amount of rapamycin orally, parenterally, intranasally, intrabronchially, or rectally.

7 Claims, No Drawings

METHOD OF TREATING SYSTEMIC LUPUS ERYTHEMATOSUS

BACKGROUND OF THE INVENTION

Systemic lupus erythematosus (SLE), an autoimmune disease primarily affecting young females, is characterized by hyperproliferation of T-lymphocytes; development of autoantibodies directed against nuclear antigens, particularly double-stranded DNA; and immune complex mediated pathology [R. Bartlett, *Scand. J. Rheum.*, 75:290 (1988 Supp.)]. Complexation of the nuclear autoantibodies with their respective antigens, which are subsequently deposited in the small blood vessels, is a direct cause of many of the clinical manifestations of SLE.

Clinical manifestations of SLE are observed in almost all organ systems [see, I. McKay, Autoimmune Diseases, Charles C.. Thomas, pub., p.70]. These typically include a facial erythematous rash with a "butterfly" distribution over the nose and cheeks. Arthritis and arthralgia most commonly affecting the phalangeal and carpal joints are observed in a majority of SLE patients. Renal involvement is observed in approximately 70% of SLE patients, and is considered to be one of the major causes of mortality from SLE. Glomerulonephritis secondary to the deposition of autoantibody-antigen complex in the kidney, often leads to renal impairment, as observed by proteinuria, or ultimately renal failure. Clinical manifestations of SLE also are observed in the lymphatic, pulmonary, gastrointestinal, hemic, vascular, and central nervous systems.

Current treatment of SLE depends on the location and severity of the disease; with the method of treatment often dictated by the organ system affected. Arthritis or arthralgias can often be controlled with aspirin or other non-steroidal anti-inflammatory drugs. More severe manifestations of SLE such as hemolytic anemia, thrombocytopenic purpura, and severe polyserositis have been treated with prednisone. Currently recommended treatment for renal impairment utilizes combinations of prednisone with immunosuppressive agents such as azathioprine or cyclophosphamide.

As none of the methods of treatment presently available are completely satisfactory, current research has focused on developing agents for the treatment of SLE. Several animal models have been utilized to study the etiology of SLE and to evaluate potential forms of treatment.

The MRL/MpJ/lpr/lpr (MRL/lpr) mouse is a standard animal model for SLE, in which the autosomal recessive allele, lpr (lymphoproliferation) is associated with severe lymphadenopathy, early auto-antibodies, circulating immune complexes, glomerulonephritis, splenomegaly, arthritic changes, pulmonary lesions [Y. Kono, *Int. J. Immunother.* (2), 149 (1986)], progressive histopathological changes including lymphocytic and monocytic cell infiltrations, and inflammation and destruction of normal tissue architecture; all which contribute to early death (6 months). These manifestations, which are at least partially caused by hyperproliferation of dysfunctional T-lymphocytes, begin to appear at approximately 8 weeks of age. The MRL/MpJ +/+ is without the recessive gene, lpr, and therefore has a normal lifespan (2 yrs) with only mild and late symptoms of arthritis and glomerulonephritis. The MRL/lpr mouse is characterized by lymphadenopathy of double negative (L3T4$^-$, Lyt-2$^-$) lymphocytes [Kotzin, J. Exp. Med. 168:2221 (1988)] which have lost the normal T cell functions of concanavalin A (Con A) responsiveness and interleukin-2 production (R. Cameron, Immunol 59: 187 (1986)]. Therefore, a growing suppression of mitogenic responsiveness and IL-2 production is seen with disease progression.

The immunosuppressants cyclosporine A (CsA) and FK-506, have been evaluated in the MRL/lpr model of SLE. A decrease in lymphadenopathy was observed in MRL/lpr mice treated with 25 mg/kg of CsA. However, at this dose there was no improvement in glomerulonephritis (as evidence by a decrease in kidney function and albuminuria), no change in anti-DNA or anti-IgG autoantibody levels, and no prolongation of lifespan [J. Berden, Scand J. Immunol. 24:405 (1986)]. At a dose of 40 mg/kg, CsA decreased lymphadenopathy, arthritis, and glomerulonephritis and increased the survival time of the MRL/lpr mice, but did not affect levels of anti-DNA autoantibodies [J. Mountz, J. Immunol. 138: 157 (1987)].

A decrease in proteinuria and the progression of neuropathy, and an increase in survival time was observed in MRL/lpr mice that were treated with 2.5 mg/kg of FK-506; however, no change in levels of anti-DNA autoantibodies were observed [K. Takabayshi, Clin. Immunol. Immunopath. 51:110 (1989)].

Rapamycin, a macrocyclic triene antibiotic produced by *Streptomyces hygroscopicus* [U.S. Pat. No. 3,929,992] has been shown to prevent the formation of humoral (IgE-like) antibodies in response to an albumin allergic challenge [Martel, R., Can. J. Physiol.. Pharm. 55:48 (1977)], inhibit murine T-cell activation [Strauch, M., FASEB 3:3411 (1989)], and prolong survival time of organ grafts in histoincompatible rodents [Morris, R., Med. Sci. Res. 17:877 (1989)].

DESCRIPTION OF THE INVENTION

This invention provides a method for arresting the development, or retarding the progression of SLE in a mammal in need thereof by administering an effective amount of rapamycin orally, parenterally, intranasally, intrabronchially, or rectally.

The effect of rapamycin on SLE was established in the MRL/lpr mouse, a standard animal model for SLE. The procedures used and results obtained are described below. CsA also was evaluated in the MRL/lpr mouse for the purpose of comparison.

Female MRL/lpr mice were treated with either rapamycin or CsA beginning in one test when the mice were 8 weeks of age (Test 1), and in a second test when the mice were 10 weeks of age (Test 2), and in a third test when the mice were 6 weeks of age (Test 3). Rapamycin was dissolved in absolute ethanol and prepared in a final formulation of 8% cremophor and 2% ethanol. CsA was obtained in a formulation containing cremophor and alcohol and was diluted with water to approximately the same concentration as the rapamycin solution. The mice in each test were dosed by gavage 3 times per week. MLR/lpr mice treated with vehicle, and untreated MRL/lpr mice, were used as controls in each of the three tests.

The following table shows the effect of rapamycin and CsA on survival time.

| EFFECT OF RAPAMYCIN AND CsA ON SURVIVAL TIME+ | | | | |
| --- | --- | --- | --- | --- |
| | Percent Survival | | | Median Survival (days) |
| Test 1 | | | | |
| Day of Study | 190 | 250 | 281 | |
| Vehicle | 33 | 27 | 13 | 162 |
| Naive | 33 | 13 | 13 | 135 |
| Rapamycin 6 mg/kg | 53 | 47 | 24 | 237 |
| Rapamycin 12 mg/kg | 80* | 60* | 52* | 283* |
| CsA 6 mg/kg | 40 | 13 | 0 | 171 |
| Test 2 | | | | |
| Day of Study | 129 | 136 | 181 | |
| Vehicle | 58 | 42 | 17 | |
| Naive | 25 | 25 | 0 | |
| Rapamycin 12.5 mg/kg | 83 | 65 | 46 | |
| Rapamycin 25 mg/kg | 92** | 92** | 55** | |
| CsA 12.5 mg/kg | 50 | 25 | 8 | |
| CsA 25 mg/kg | 25 | 8 | 8 | |

+Test 1 based on 15 mice per group and test 2 based on 12 mice per group.
*Significantly (p < 0.03) longer survival than vehicle-treated mice.
**Significantly (p < 0.05) longer survival than vehicle-treated mice.

These data demonstrate that rapamycin, at a dose of 12 mg/kg in Test 1 and at a dose of 25 mg/kg in Test 2, significantly increased the survival time of MRL/lpr mice when compared with MRL/lpr mice treated only with vehicle. The percent survival of mice treated with rapamycin at each time period also was greater than that was observed in mice treated with CsA.

Anti-DNA antibody levels were determined by radioimmunoassay in mice that were evaluated in Test 2. Blood was drawn at age 10 weeks and at 4 week periods thereafter. Sera (25 µl) was incubated with 200 µl DNA-$I^{125}$ for 2 hours at 37° in a shaking water bath. Ammonium sulfate (1 ml) was added to each tube and the tubes were vortexed. Each tube was centrifuged for 15 m in at 2000×g; the supernatant was aspirated and the precipitate was counted in a gamma counter. The quantity of anti-double stranded DNA antibodies was determined from a standard curve.

The following table shows the results obtained for MRL/lpr mice treated with rapamycin or CsA.

| MEAN ANTI-DNA ANTIBODY LEVELS | | |
| --- | --- | --- |
| | Units/ml | |
| | 10 weeks | 18 weeks |
| Vehicle | 53 | 183 |
| Naive | 34 | 211 |
| Rapamycin 12.5 mg/kg | 28 | 68* |
| Rapamycin 25 mg/kg | 49 | 63* |
| CsA 12.5 mg/kg | 58 | 91 |
| CsA 25 mg/kg | 28 | 240 |

*No change from prebleed level.

In the MRL/lpr mouse, manifestations of SLE begin to occur at approximately 8 weeks and develop progressively. These data show that rapamycin prevented the elevation of anti-DNA antibody levels that were observed in control or CsA-treated MRL/lpr mice.

The effect of rapamycin on renal function was evaluated by measuring urinary albumin in the MRL/lpr mice used in Test 2. Elevated urinary albumin levels are indicative of renal impairment. The following procedure was used. Urine was obtained from the MRL/lpr mice at age 10 weeks and monthly thereafter. The urine was diluted 1:20 in sterile water, and 200 µl of bromocresol green was added to 100 µl urine solution. The absorbance was read at 630 nm. A standard solution of albumin was treated similarly. The quantity of urinary albumin was determined from a standard curve.

The following table shows the levels of urinary albumin in MRL/lpr mice treated with rapamycin or CsA.

| MEAN URINARY ALBUMIN LEVELS (µg/ml) | | |
| --- | --- | --- |
| | Age 10 weeks | Last Sample Observed+ |
| Vehicle | 540 | 3253 |
| Naive | 596 | 3406 |
| Rapamycin 12.5 mg/kg | 786 | 879 |
| Rapamycin 25 mg/kg | 974 | 764 |
| CsA 12.5 mg/kg | 699 | 837 |
| CsA 25 mg/kg | 764 | 712 |

+Mean of the last monthly urine sample obtained for each mouse.

The results demonstrate that rapamycin prevented the development of glomerular nephritis in the MRL/lpr mouse as evidenced by urinary albumin levels that were not elevated significantly above levels observed when the MRL/lpr mice were 10 weeks of age. Similar results were observed in the MRL/lpr mice treated with CsA. Urinary albumin levels of untreated mice significantly increased concomitant with disease progression.

The effect of rapamycin on preventing lymphadenopathy and splenomegaly, that are observed with SLE, was determined in the MRL/lpr mice used in Test 3. After 2 months of treatment with rapamycin, CsA, or vehicle, the mice were humanly sacrificed by asphyxiation with $CO_2$. The spleen, inguinal, and axillary lymph nodes were removed. The spleens were weighed and the diameters of the lymph nodes were measured immediately. An end section of the spleen was used for histology, and the middle section was used in standard pharmacological test procedures for splenocyte proliferation and interleukin 2 (IL-2) production.

The following tables shows the effects of rapamycin and CsA on lymph node diameters.

| MRL/lpr MOUSE LYMPH NODE DIAMETERS | | | | |
| --- | --- | --- | --- | --- |
| Treatment | L. Ing. | R. Ing. | L Axil | R. Axil |
| Naive | 6.9 ± 0.3 | 6.5 ± 0.6 | 10.8 ± 0.7 | 11.0 ± 0.7 |
| Vehicle | 5.0 ± 0.5 | 4.9 ± 0.5 | 9.3 ± 0.7 | 10.0 ± 0.6 |
| Rapamycin 12.5 mg/kg | 3.0 ± 0.3 | 2.4 ± 0.3 | 3.5 ± 0.4 | 4.1 ± 0.3 |
| Rapamycin 25 mg/kg | 2.9 ± 0.2 | 2.7 ± 0.2 | 3.9 ± 0.2 | 4.1 ± 0.2 |
| CsA 12.5 mg/kg | 7.9 ± 0.9 | 5.6 ± 0.6 | 10.3 ± 0.8 | 11.0 ± 0.7 |
| CsA 25 mg/kg | 6.9 ± 0.4 | 5.8 ± 0.6 | 10.0 ± 0.4 | 9.9 ± 0.6 |

These results demonstrate that rapamycin prevented the enlargement of lymph nodes which is associated with the lymphadenopathy caused by SLE. CsA did not prevent the enlargement of the lymph nodes and provided similar results to naive and vehicle-treated MRL/lpr mice.

The following tables shows the effect of rapamycin and CsA on spleen weight.

| MRL/lpr MOUSE SPLEEN WEIGHTS | |
| --- | --- |
| Treatment | Grams |
| Naive | 0.41 ± 0.07 |
| Vehicle | 0.28 ± 0.03 |
| Rapamycin 12.5 mg/kg | 0.19 ± 0.01 |
| Rapamycin 25 mg/kg | 0.14 ± 0.00 |
| CsA 12.5 mg/kg | 0.38 ± 0.03 | splenocyte proliferation standard pharmacological test procedure.

| | MRL/lpr SPLENOCYTE PROLIFERATION* | | | | |
|---|---|---|---|---|---|
| | | Mitogen | | | |
| | No. Mitogen | Con A | PHA | LPS | PMA |
| Naive | 0.75 ± 0.1 | 3.58 ± 0.8 | 23.54 ± 4.0 | 7.01 ± 1.7 | 3.63 ± 0.4 |
| Vehicle (control) | 1.05 ± 0.1 | 6.04 ± 0.7 | 33.19 ± 2.1 | 10.14 ± 1.5 | 3.66 ± 0.3 |
| Rapamycin 12.5 mg/kg | 1.54 ± 0.1 | 27.25 ± 2.1 | 41.73 ± 1.5 | 24.32 ± 1.9 | 4.49 ± 0.3 |
| Rapamycin 25 mg/kg | 2.54 ± 0.3 | 38.12 ± 2.7 | 45.88 ± 1.8 | 22.69 ± 1.8 | 5.11 ± 1.3 |
| CsA 12.5 mg/kg | 1.13 ± 0.0 | 5.74 ± 1.3 | 31.75 ± 1.8 | 8.78 ± 2.2 | 3.49 ± 0.2 |
| CsA 25 mg/kg | 2.22 ± 0.2 | 7.14 ± 1.0 | 39.91 ± 1.3 | 16.32 ± 3.2 | 4.33 ± 0.3 |
| MRL/+/+ mouse | 1.27 ± 0.1 | 48.82 ± 4.2 | 59.11 ± 3.5 | 44.93 ± 2.0 | 4.45 ± 0.4 |

*Results expressed in counts per minute × 1000

| MRL/lpr MOUSE SPLEEN WEIGHTS | |
|---|---|
| Treatment | Grams |
| CsA 25 mg/kg | 0.30 ± 0.02 |

These results demonstrate that rapamycin prevented the enlargement of the spleen which is associated with the splenomegaly caused by SLE. CsA did not prevent the enlargement of the spleen, and provided results similar to untreated MRL/lpr mice or mice treated with vehicle.

The progression of SLE is accompanied by a decrease in the proliferation of splenocytes in response to mitogens. In the MRL/lpr mouse, this corresponds to a diminished splenocyte proliferation in response to mitogens such as concanavalin A (Con A), lipopolysaccaride (LPS), phytohemagglutinin (PHA), and phorbol myristic acid (PMA). The effect of rapamycin and CsA on splenocyte proliferation in the MRL/lpr mice used in Test 3 was evaluated in an ex vivo spleen cell proliferation standard pharmacological test procedure. The MRL +/+ mouse, the wild strain that develops only mild SLE symptoms because of the absence of the lpr gene, also was used as a control to determine normal levels of splenocyte proliferation in response to the mitogens.

The following standard test procedure was used. Spleens were removed under sterile conditions and pressed through a stainless steel 500 mesh screen to produce a single cell suspension. Erythrocytes were lysed by incubating cells for four minutes in 0.83% w/v ammonium chloride and cells were immediately washed twice with RPMI 1640 ® medium. Spleen cells were resuspended to a concentration of $5 \times 10^6$ cells/ml in RPMI 1640 ® medium containing 10% fetal calf serum, 100 units/ml penicillin, 100 µg/ml streptomycin, 2 mM 1-glutamine, 0.1 mM non-essential amino acids, 1 mM sodium pyruvate, and $5 \times 10^{-5}$ M 2-mercaptoethanol. Cells were incubated at 37° C. in 5% $CO_2$ in 96-well microtiter plates at a concentration of $5 \times 10^5$ cells/well for a total of 72 hours. Mitogens were diluted to the appropriate concentrations in the medium described above, and added to the wells at the beginning of the incubation period to give a final concentration of 2.0 µg/ml Con A, 10 µg/ml LPS, 10 µg/ml PHA or 10 ng/ml PMA in a final volume of 0.2 ml. Spontaneous proliferation (no mitogen) was also assessed. Proliferation in wells was assessed by [$^3$H] thymidine incorporation (1 µCi/ml) during the last 18 hours of incubation. Six animals per group were separately analyzed in culture, with six wells per animal plated and the counts per minute were averaged for each group.

The following table shows the results obtained for MRL/lpr mice treated with rapamycin or CsA in the splenocyte proliferation standard pharmacological test procedure.

These results demonstrate that rapamycin prevented the diminished ability to proliferate in response to mitogens that is associated with the progression of SLE. Splenocytes from CsA-treated animals showed only partially restored response to PHA and LPS stimulation.

Concomitant with the development of SLE is the loss of the ability to produce interleukin 2 (IL-2). This manifestation is also observed in the MRL/lpr mouse. The effect of rapamycin and CsA on IL-2 production in the MRL/lpr mice used in Test 3 was evaluated in an ex vivo standard pharmacological test procedure using a CTTL-2 cell bioassay. The MRL +/+ mouse was used as a control to determine normal levels of IL-2 production. The following procedure was used to measure IL-2 production.

Spleen cell cultures from the same animals used in the spelocyte proliferation standard test procedure described above were treated in the same manner as described in that procedure except that only the mitogen Con A was used. Cells were incubated at 37° C. in 5% $CO_2$ in 96-well microtiter plates for 24 hours. Supernatants were collected (600 µl/sample) and IL-2 content was determined as follows. CTLL-2 cells were grown in 75 cm$^2$ tissue culture flasks, and were split twice a week. Each flask contained a total of 25 ml RPMI 1640 medium with 2 mM sodium Pyruvate, 2 mM 1-glutamine, 15 mM hepes, 8% fetal calf serum, 100 units/ml penicillin, 100 µg/ml streptomycin, and 5-30 units per ml of recombinant human IL-2 (rhIL-2). Cells were seeded at 1:100 or 1:50 dilution from a healthy culture. Healthy cultures were harvested and centrifuged at 1000 rpm for 10 minutes. The spent medium was removed and the cells resuspended in assay medium (CTLL-2 maintenance medium minus rhIL-2). The cells were washed a second time (to remove all residual IL-2) at 1000 rpm for 10 minutes. The supernatant was discarded and the cells resuspended in fresh assay medium at $5 \times 10^4$/ml. The wells of a 96-well microtiter plate were first filled with 100 µl of sample to be tested (done in triplicate). The standard curve was set up by filling the appropriate wells with 100 µl of assay medium, and then 100 µl of rhIL-2 were added to the first well of each column (also done in triplicate). Two-fold serial dilutions were made down the plate, the last 100 µl being discarded. The standard curve started at 50 units/ml final concentration of rhIL-2 and eight two-fold dilutions were made. Triplicate wells of medium alone were set. When all samples and controls were in place, 100 µl of cell suspension were added to each well. The plate was incubated at 37° C. in 5% $CO_2$ overnight or 20 to 24 hours. The plate was then pulsed with tritiated thymidine, 20 µl/well, to give a final concentration of 1 μCi/ml. The plate was incubated for an additional 8 hours and the cells harvested onto glass fiber filters which were then deposited into scintillation vials. The vials were filled with 2 ml of scintillation fluid and counted for one minute each on a beta counter. Counts per minute were recorded.

The results obtained in the ex vivo IL-2 production standard pharmacological test procedure are provided in the following table.

| MRL/lpr IL-2 PRODUCTION* | | |
|---|---|---|
| | CPM | U/ml |
| Naive | 2706 ± 546 | 0.191 ± 0.031 |
| Vehicle | 3531 ± 610 | 0.238 ± 0.035 |
| Rapamycin 12.5 mg/kg | 9166 ± 602 | 0.562 ± 0.037 |
| Rapamycin 25 mg/kg | 8317 ± 1516 | 0.535 ± 0.106 |
| CsA 12.5 mg/kg | 2573 ± 687 | 0.174 ± 0.042 |
| CsA 25 mg/kg | 2438 ± 485 | 0.168 ± 0.032 |
| MRL +/+ mouse | 13775 ± 1273 | 0.955 ± 0.144 |

*Results expressed in counts per minute (CPM) and Units per millimeter (U/ml)

These results demonstrate that rapamycin prevented the diminution in IL-2 production in response to Con A that is associated with SLE. CsA had no positive effect on IL-2 production as compared with MRL/lpr mice treated with vehicle.

Histologic examination was conducted on the heart, lung, trachea, two inguinal and two axillary lymph nodes, spleen, liver, both kidneys with adrenals, and thymus of MRL/lpr mice that were evaluated in Test 3 following 2 months of treatment. Tissue sections were stained with hematoxylin and eosin. Histologic changes in the MRL/lpr mouse are representative of the changes seen in humans with SLE. The effects of rapamycin and CsA on histologic changes associated with SLE are described below.

Focal peribronchial or perivascular mononuclear cell infiltration in the lung is a common finding in the MRL/lpr mouse. In the naive control mice the incidence of this change was 100%, however, rapamycin significantly reduced the incidence and severity of this change in the lung of these mice. CsA at 12.5 and 25 mg/kg significantly worsened the focal perviascular mononuclear cell infiltration.

Inflammatory changes noted in the liver, such as focal periportal or perivascular inflammatory cell infiltration, focal inflammation and focal vasculitis were reduced in incidence in all rapamycin and CsA-treated groups when compared with the vehicle-treated or naive group. Rapamycin at both doses significantly reduced periportal inflammatory cell infiltration.

Lymphoid hyperplasia is characterized by an increase in the number of lymphoid cells and/or size of lymphoid follicles. All animals in groups naive, vehicle, CsA at 12.5 mg/kg, and CsA at 25 mg/kg revealed lymphoid hyperplasia in the spleen, lymph nodes and thymus. The severity of this change was similar in all affected groups. Rapamycin treated animals did not reveal lymphoid hyperplasia in the spleen and thymus, however, 1 mouse in the 25 mg/kg rapamycin group showed this change in the lymph node.

Both doses of rapamycin significantly reduced focal periportal inflammatory cell infiltration. In the kidneys, both doses of rapamycin significantly reduced focal vasculitis, focal pyelitis, and focal interstitial nephritis. CsA 25 at mg/kg significantly worsened focal fasculitis and focal pyelitis. Both doses of CsA significantly reduced interstitial nephritis. The naive group had significantly higher scores than the vehicle for focal pyelitis and significantly lower scores than the vehicle for focal interstitial nephritis.

Focal vacuolation in the cortex of adrenals is a common finding in the MRL/lpr mouse; however, both dose levels of rapamycin reduced the incidence of focal vacuolation significantly.

The results of histologic examination of organs typically affected by SLE demonstrated that rapamycin prevented adverse histologic changes indicative of the progression of SLE.

In summary, results of these standard pharmacological test procedures using the MRL/lpr mouse, a standard animal model for human SLE, demonstrate that rapamycin is useful for arresting the development and retarding the progression of SLE in a mammal by virtue of its ability to increase survival time of the MRL/lpr mouse, prevent the elevation of urinary albumin and anti-DNA autoantibody levels, prevent the diminution of splenocyte proliferation and IL-2 production in response to mitogens, and arrest histomorphological changes associated with the progression of SLE.

When rapamycin is employed for arresting the development or retarding the progression of SLE, it can be formulated into oral dosage forms such as tablets, capsules and the like. Rapamycin can be administered alone or by combining it with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, table-disintegrating agents and the like may be employed. Rapamycin may be encapsulated with or without other carriers. In all cases, the proportion of active ingredients in said compositions both solid and liquid will be at least to impart the desired activity thereto on oral administration. Rapamycin may be injected parenterally, in which case it is used in the form of a sterile solution containing other solutes, for example, enough saline or glucose to make the solution isotonic. Rapamycin also may be administered rectally in the form of a conventional suppository. For administration by intranasal or intrabronchial inhalation or insufflation, rapamycin may be formulated into an aqueous or partially aqueous solution, which can then be utilized in the form of an aerosol.

The dosage requirements vary with the particular compositions employed, the route of administration, the severity of the symptoms presented and the particular subject being treated. Based on the results obtained in the standard pharmacological test procedures, projected oral daily dosages of active compound would be 0.01-75 mg/kg, preferably between 0.1-50 mg/kg, and more preferably between 1-50 mg/kg. Projected parenteral daily dosages of active compound would be 0.01-50 mg/kg, preferably between 0.1-10 mg/kg, and more preferably between 0.1-1 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. In general, rapamycin is most desirably administered at a concentration that will generally afford effective results without causing any harmful or deleterious side effects, and can be administered either as a single unit dose, or if desired, the dosage may be divided into convenient subunits administered at suitable times throughout the day.

What is claimed is:

1. A method of arresting the development or retarding the progression of systemic lupus erythematosus in a mammal in need thereof which comprises administering to said mammal a lupus arresting or retarding amount of rapamycin orally, parenterally, intranasally, intrabronchially, or rectally.

2. The method of claim 1, which comprises administering rapamycin orally in a daily dose of 0.01 to 75 mg/kg.

3. The method of claim 1, which comprises administering rapamycin orally in a daily dose of 0.1 to 50 mg/kg.

4. The method of according to claim 1, which comprises administering rapamycin orally in a daily dose of 1 to 50 mg/kg.

5. The method according to claim 1, which comprises administering rapamycin parenterally in a daily dose of 0.01 to 50 mg/kg.

6. The method according to claim 1, which comprises administering rapamycin parenterally in a daily dose of 0.1 to 10 mg/kg.

7. The method according to claim 1, which comprises administering rapamycin parenterally in a daily dose of 0.1 to 1 mg/kg.

* * * * *